(12) United States Patent
Bao et al.

(10) Patent No.: US 11,813,013 B2
(45) Date of Patent: Nov. 14, 2023

(54) VARIABLE CRYOSURGICAL PROBE PLANNING SYSTEM

(71) Applicant: Varian Medical Systems, Inc., Palo Alto, CA (US)

(72) Inventors: Shenghao Bao, Ladera Ranch, CA (US); Jay J. Eum, Irvine, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 299 days.

(21) Appl. No.: 17/176,955

(22) Filed: Feb. 16, 2021

(65) Prior Publication Data

US 2021/0161580 A1 Jun. 3, 2021

Related U.S. Application Data

(63) Continuation of application No. 15/669,943, filed on Aug. 6, 2017, now Pat. No. 10,952,784, which is a (Continued)

(51) Int. Cl.
*A61B 34/10* (2016.01)
*A61B 18/02* (2006.01)
(Continued)

(52) U.S. Cl.
CPC ........ *A61B 18/0218* (2013.01); *A61B 5/0008* (2013.01); *A61B 5/01* (2013.01);
(Continued)

(58) Field of Classification Search
CPC .......... A61B 2018/00005; A61B 2018/00011; A61B 2018/00505; A61B 2018/00511; A61B 2018/00517; A61B 2018/00529; A61B 2018/00541; A61B 2018/00547; A61B 2018/00744; A61B 2018/00982; A61B 8/08; A61B 8/0833; A61B 8/0841; A61B 8/085; A61B 8/0858; A61B 8/4245; A61B 8/5238; A61B 8/5246; A61B 8/5253; A61B 34/10; A61B 2034/101; A61B 2034/104; A61B 2034/107; A61B 2034/108; A61B 18/02; A61B 18/0212;
(Continued)

(56) References Cited

U.S. PATENT DOCUMENTS 4,672,963 A 6/1987 Barken
5,531,742 A 7/1996 Barken
(Continued)

*Primary Examiner* — Ahmed M Farah
(74) *Attorney, Agent, or Firm* — Duane Morris LLP

(57) ABSTRACT

A cryosurgical system including a computer system programmed with software configured to perform the following steps: a) capturing at least one first view of a region of interest in a human body; b) capturing at least one second view of the region of interest; c) outlining the region of interest and at least one area outside the region of interest with the assistance of an operator; d) constructing a 3-dimensional model of the region of interest and the at least one area outside the region of interest utilizing the at least one first view and the at least one second view of the region of interest; and e) utilizing the 3-dimensional model of the region of interest and the at least one area outside the region of interest to determine at least one cryosurgical probe placement location.

20 Claims, 10 Drawing Sheets

Related U.S. Application Data continuation of application No. 13/731,639, filed on Dec. 31, 2012, now Pat. No. 9,724,150, which is a continuation of application No. 13/481,557, filed on May 25, 2012, now Pat. No. 8,562,593, which is a continuation of application No. 11/618,492, filed on Dec. 29, 2006, now Pat. No. 8,187,260.

(51) Int. Cl.

| | | |
|---|---|---|
| *A61B 5/01* | (2006.01) | |
| *A61B 8/08* | (2006.01) | |
| *A61B 5/00* | (2006.01) | |
| *A61B 8/00* | (2006.01) | |
| *A61B 18/00* | (2006.01) | |
| *A61B 17/00* | (2006.01) | |
| *A61B 90/00* | (2016.01) | |

(52) U.S. Cl.
CPC ............ *A61B 8/085* (2013.01); *A61B 8/0841* (2013.01); *A61B 8/0858* (2013.01); *A61B 8/4254* (2013.01); *A61B 8/4263* (2013.01); *A61B 8/4416* (2013.01); *A61B 8/5223* (2013.01); *A61B 8/5238* (2013.01); *A61B 8/5253* (2013.01); *A61B 8/546* (2013.01); *A61B 34/10* (2016.02); *A61B 18/02* (2013.01); *A61B 2017/00274* (2013.01); *A61B 2018/00011* (2013.01); *A61B 2018/00511* (2013.01); *A61B 2018/00529* (2013.01); *A61B 2018/00547* (2013.01); *A61B 2018/00744* (2013.01); *A61B 2018/00761* (2013.01); *A61B 2018/00791* (2013.01); *A61B 2018/00982* (2013.01); *A61B 2034/104* (2016.02); *A61B 2090/378* (2016.02)

(58) Field of Classification Search
CPC ............ A61B 18/0218; A61B 18/0262; A61B 18/0293; A61B 17/00234; A61B 17/00274

USPC .................................. 606/1, 20–26; 600/424
See application file for complete search history.

(56) References Cited

U.S. PATENT DOCUMENTS

| | | | |
|---|---|---|---|
| 5,706,810 A | 1/1998 | Rubinsky et al. | |
| 5,800,487 A | 9/1998 | Mikus et al. | |
| 6,074,412 A | 6/2000 | Mikus et al. | |
| 6,139,544 A | 10/2000 | Mikus et al. | |
| 6,142,991 A | 11/2000 | Schatzberger | |
| 6,206,832 B1 | 3/2001 | Downey | |
| 6,423,009 B1 | 7/2002 | Downey | |
| 6,512,942 B1 | 1/2003 | Burdette et al. | |
| 6,610,013 B1 | 8/2003 | Fenster et al. | |
| 6,643,535 B2 | 11/2003 | Damasco et al. | |
| 6,694,170 B1 * | 2/2004 | Mikus .................... | A61B 18/02 600/407 |
| 6,905,492 B2 | 6/2005 | Zvuloni | |
| 7,831,076 B2 * | 11/2010 | Altmann ................ | A61B 5/743 382/128 |
| 7,909,227 B2 | 3/2011 | Duong et al. | |
| 7,996,060 B2 * | 8/2011 | Trofimov ............... | A61B 5/283 382/128 |
| 8,094,894 B2 | 1/2012 | Nagler et al. | |
| 8,187,260 B1 | 5/2012 | Bao et al. | |
| 8,971,597 B2 | 3/2015 | Zhao et al. | |
| 9,724,150 B1 | 8/2017 | Bao et al. | |
| 10,039,525 B2 * | 8/2018 | Yoshiara ............... | A61B 8/0841 |
| 10,952,784 B2 * | 3/2021 | Bao ....................... | A61B 8/0841 |
| 2004/0044295 A1 | 3/2004 | Reinert et al. | |
| 2004/0267248 A1 | 12/2004 | Duong et al. | |
| 2005/0010200 A1 | 1/2005 | Damasco et al. | |
| 2005/0143651 A1 | 6/2005 | Verard et al. | |
| 2005/0192565 A1 | 9/2005 | Eum et al. | |
| 2006/0264752 A1 * | 11/2006 | Rubinsky .............. | A61N 1/0412 606/41 |
| 2007/0038223 A1 | 2/2007 | Marquart et al. | |
| 2008/0004603 A1 | 1/2008 | Larkin et al. | |
| 2008/0147055 A1 | 6/2008 | Duong et al. | |
| 2023/0117915 A1 * | 4/2023 | Nouri .................... | G06V 10/454 600/437 |

\* cited by examiner

SAGITTAL VIEW

TOP VIEW

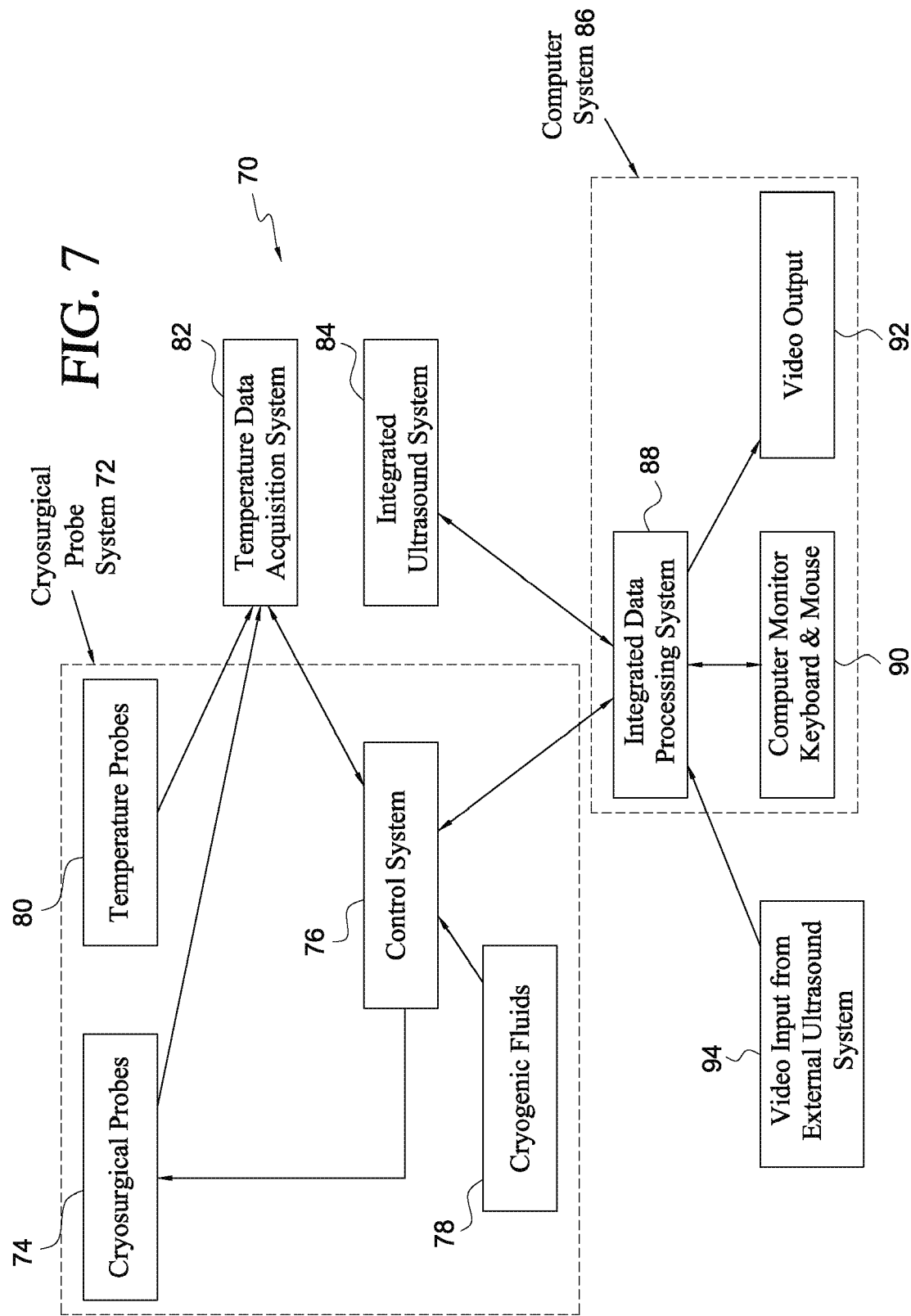

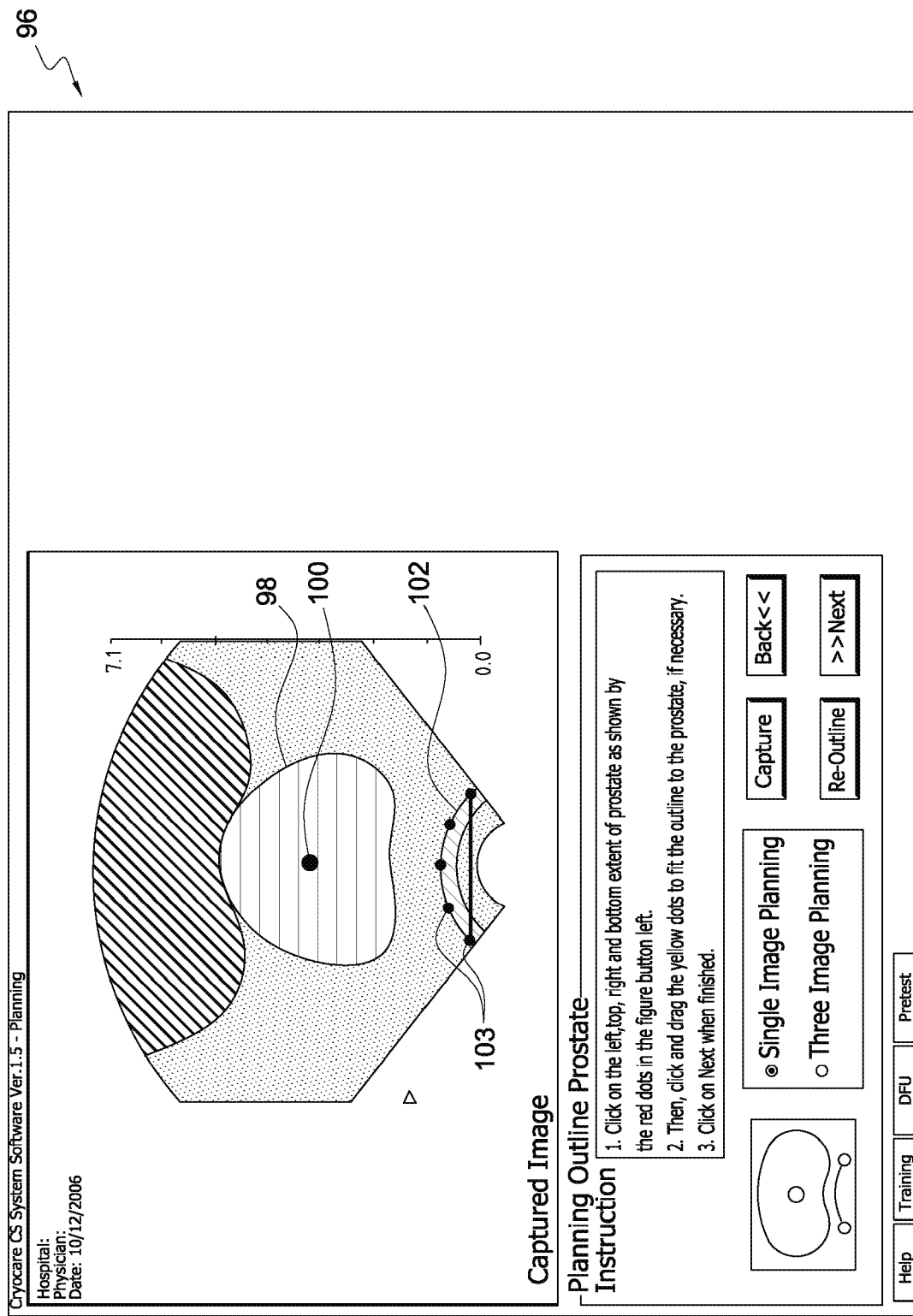

FIG. 9

Cryocare CS System Software Ver.2.8 - Placement

Hospital:
Patient:
Physician:
Date: 10/12/2006

LIVE

Placement: CryoProbe/TempProbe

1. Place TempProbes according to step 1.
2. Place CryoProbes according to step 2.
3. Place warming catheter according to step 3.
4. When all probes are placed, click Next button.

Order
- ● Post -> Ant
- ○ Ant -> Post

☑ Graphics     Back<<     >>Next

Step 1 - TempProbe Placement

| Order  | TempProbe | Grid  | Temp(°C) |
|--------|-----------|-------|----------|
| First  | ANT / C   | f 6.0 | 25.0     |
| Second | ES / F    | f 3.0 | 24.0     |
| Third  | DEN / A   | f 1.5 | OPEN     |
| Fourth | LNVB / D  | h 2.0 | 24.0     |
| Fifth* | RNVB / B  | D 2.0 | 23.0     |
| Sixth**| APEX / E  | f 2.5 | 24.0     |

Note: * See step 3 for placing ES.
** APEX is optional.

Step 2 - CryoProbe Placement

| Order   | CryoProbe | Grid  | V-Ice | Medium ▼ |
|---------|-----------|-------|-------|----------|
|         |           |       |       | Long     |
|         |           |       |       | Medium   |
|         |           |       |       | Short    |
| First   | Probe 1   | E 5.0 | M     | ON       |
| Second  | Probe 2   | H 5.0 | M     | OFF      |
| Third   | Probe 3   | D 3.0 | L     | OFF      |
| Fourth  | Probe 4   | h 3.0 | L     | OFF      |
| Fifth   | Probe 5   | e 2.5 | S     | OFF      |
| Sixth   | Probe 6   | G 2.5 | S     | OFF      |
| Seventh | Probe 7   | N/A   | N/A   | OFF      |
| Eighth  | Probe 8   | N/A   | N/A   | OFF      |

Note: * Depth guidance is for sagittal view only

Step 3 - Cystoscope & Warmer Placement

| Order  | Operations |
|--------|------------|
| First  | Perform cystoscope to ensure no TempProbes or CryoProbes are in the urethra |
| Second | Perform cystoscope to look for correct ES TempProbe placement |
| Third  | Insert guidewire through cystoscope, then remove cystoscope |
| Fourth | Insert urethra warming catheter over guidewire |

Help | Training | User Manual | Pretest | Reassign Port | Measure | Patient Info

VARIABLE CRYOSURGICAL PROBE PLANNING SYSTEM

CROSS REFERENCE TO RELATED APPLICATIONS

This is a continuation of U.S. application Ser. No. 15/669,943, entitled "Variable Cryosurgical Probe Planning System," filed on Aug. 6, 2017, which is a continuation of U.S. application Ser. No. 13/731,639, entitled "Variable Cryosurgical Probe Planning System," filed on Dec. 31, 2012 and issued Aug. 8, 2017 as U.S. Pat. No. 9,724,150, which is a continuation of U.S. application Ser. No. 13/481,557, entitled "Variable Cryosurgical Probe Planning System," filed on May 25, 2012, issued Oct. 22, 2013 as U.S. Pat. No. 8,562,593, which is a continuation of U.S. application Ser. No. 11/618,492, entitled "Variable Cryosurgical Probe Planning System," filed on Dec. 29, 2006, issued May 29, 2012 as U.S. Pat. No. 8,187,260. The entire contents of each of the above applications are incorporated herein by reference for all purposes in their entirety.

BACKGROUND OF THE INVENTION

1. Field of the Invention

Embodiments of the present invention relate to computer guided cryosurgery and more particularly to a system for assisting an operator in placing and operating at least one cryosurgical probe in a region of interest in a human patient.

2. Description of the Related Art

Cryosurgery involving the use of cryosurgical probe assemblies typically involves the use of cryoprobes that are each attached to a handle that are, in turn, connected to a high-pressure fluid line attached to a fluid source. Cryosurgical ablation of the prostate has generally required relatively small iceballs, i.e. 4 cm diameter by 6 cm length. For other applications, for example, renal applications, relatively larger iceballs are desired. Many other potential applications of cryosurgery may also require larger iceballs such as to ablate renal tumors, hepatic tumors, and pulmonary and thoracic tumors. Relatively large iceballs may also be required for palliative intervention.

The ultimate goal in a cryosurgical procedure is to freeze all tumor tissue by lethal ice to kill the tumor and not to freeze any benign tissue surrounding the tumor tissue by lethal ice to avoid complications. Due to variations of tumor size and shape, it has always been a great challenge for a cryosurgeon to precisely place multiple cryosurgical probes into desired locations of a tumor and control them so as to generate an optimum lethal iceball that is tailored to fit the tumor.

SUMMARY OF THE INVENTION

In a broad aspect, embodiments of the present invention relate to a cryosurgical system for assisting an operator in placing and operating at least one cryosurgical probe in a region of interest in a human patient. The cryosurgical system includes a computer system being programmed with software configured to perform the following steps:
  a) capturing at least one first view of a region of interest in a human body;
  b) capturing at least one second view of the region of interest;
  c) outlining the region of interest and at least one area outside the region of interest with the assistance of an operator;
  d) constructing a 3-dimensional model of the region of interest and the at least one area outside the region of interest utilizing the at least one first view and at least one second view of the region of interest; and,
  e) utilizing the 3-dimensional model of the region of interest and the at least one area outside the region of interest to determine at least one cryoprobe placement location.

Another embodiment of the present invention is directed to a cryosurgical system for assisting an operator in placing and operating at least one cryosurgical probe in a region of interest in a human patient, the system comprising:
  the at least one cryosurgical probe; and
  a computer system configured to perform the following steps:
  a) capture a first view of the region of interest;
  b) capture a second view of the region of interest;
  c) outline the region of interest and an area outside the region of interest utilizing the first view and the second view of the region of interest;
  d) construct a 3-dimensional model of the region of interest and the area outside the region of interest utilizing the first view and the second view of the region of interest; and
  e) utilize the 3-dimensional model of the region of interest and the area outside the region of interest to determine i) the number of cryosurgical probes to be utilized; ii) cryosurgical probe settings; and iii) cryosurgical probe placement locations.

A further embodiment of the present invention is directed to a cryosurgical system for assisting an operator in placing and operating at least one cryosurgical probe in a first area of a human patient, the system comprising:
  a computer system programmed with software configured to perform the following steps:
  a) capturing a plurality of first views of the first area;
  b) capturing a second view of the first area;
  c) outlining the first area and at least one second area of the human patient;
  d) constructing a 3-dimensional model of the first area and the second area utilizing the plurality of first views and the second view of the first area;
  e) utilizing the 3-dimensional model of the first area and the second area to determine at least one cryosurgical probe placement location; and
  f) providing a graphical overlay on an ultrasound image for directing cryosurgical probe placement.

The resultant ice thus produced by the cryosurgical probes is optimized for a specific patient.

Although the present inventive principles will be discussed in detail with respect to their application to the prostate they may have many additional applications. Some additional particular applications include ablation of renal tumors, hepatic tumors, and pulmonary and thoracic tumors. Relatively large iceballs may also be required for palliative intervention. Such additional applications involve the selection of regions of interest and subregions within these regions in order to provide the modeling.

BRIEF DESCRIPTION OF THE DRAWINGS

FIG. 7 is a block diagram of a preferred embodiment of the cryosurgical system of the present invention.

FIG. 8 is an example screen display showing a captured image of the outline of the middle gland of the prostate on the transverse view.

FIG. 9 is an example screen display showing the utilization of the depth guide of the present invention.

DETAILED DESCRIPTION OF THE INVENTION

Figure 1:
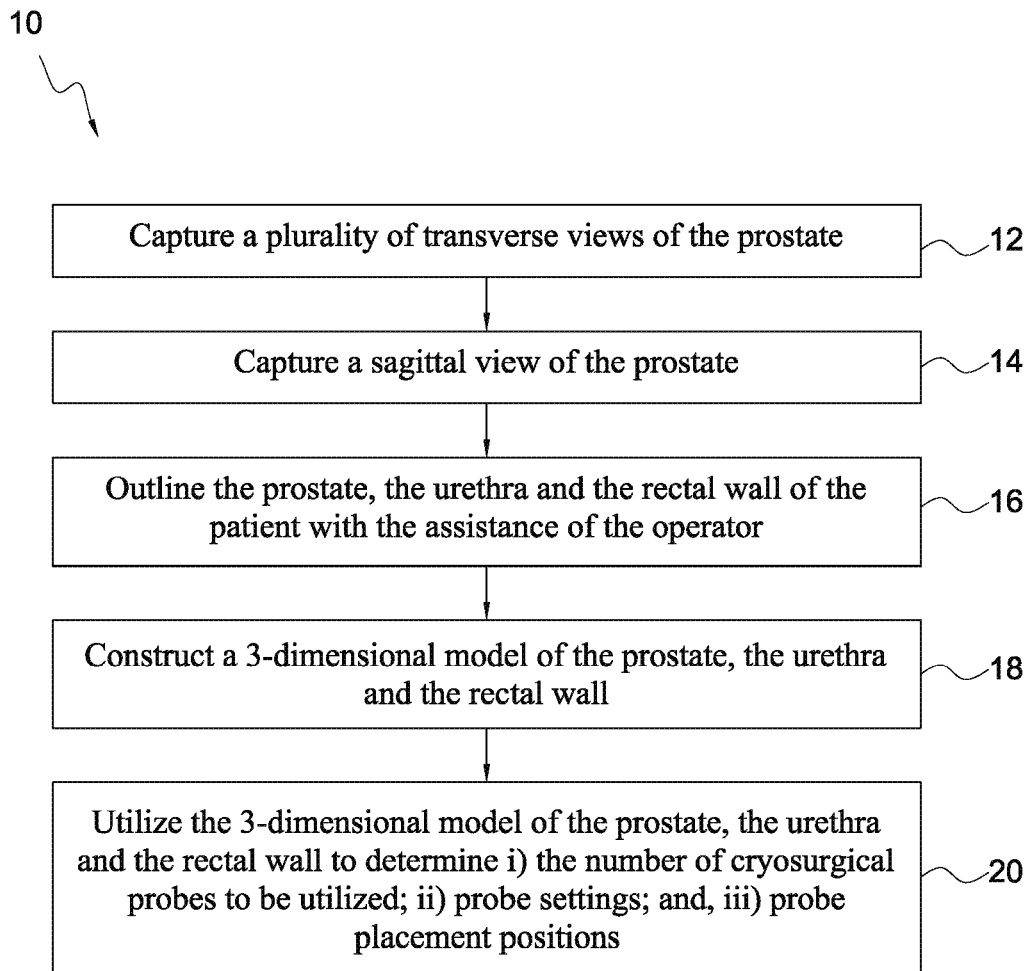
FIG. 1 is a flow chart illustrating, in a broad aspect, the steps implemented by the software of the computer system of the cryosurgical system of the present invention.

Referring now to the drawings and the characters of reference marked thereon, FIG. 1 illustrates, in a broad aspect, the steps implemented by the computer system of the present invention to optimize usage of cryosurgical probes for a specific patient. These steps are designated generally as 10. In a first step, the computer system captures a plurality of transverse views of the prostate, as noted by numeral designation 12. It then captures a sagittal view of the prostate (process block 14). The capsule of the prostate, the urethra and the rectal wall of the patient are outlined with the assistance of the operator, utilizing the captured plurality of transverse views and the captured sagittal view (process block 16). A 3-dimensional model of the prostate, the urethra and the rectal wall is constructed utilizing the outlines noted above (process block 18). The 3-dimensional model is used to determine i) the number of cryosurgical probes to be utilized; ii) probe settings; and, iii) probe placement positions (process block 20). The computer system used may be, for example, a PC running on the Microsoft Windows operating system.

Figure 2:
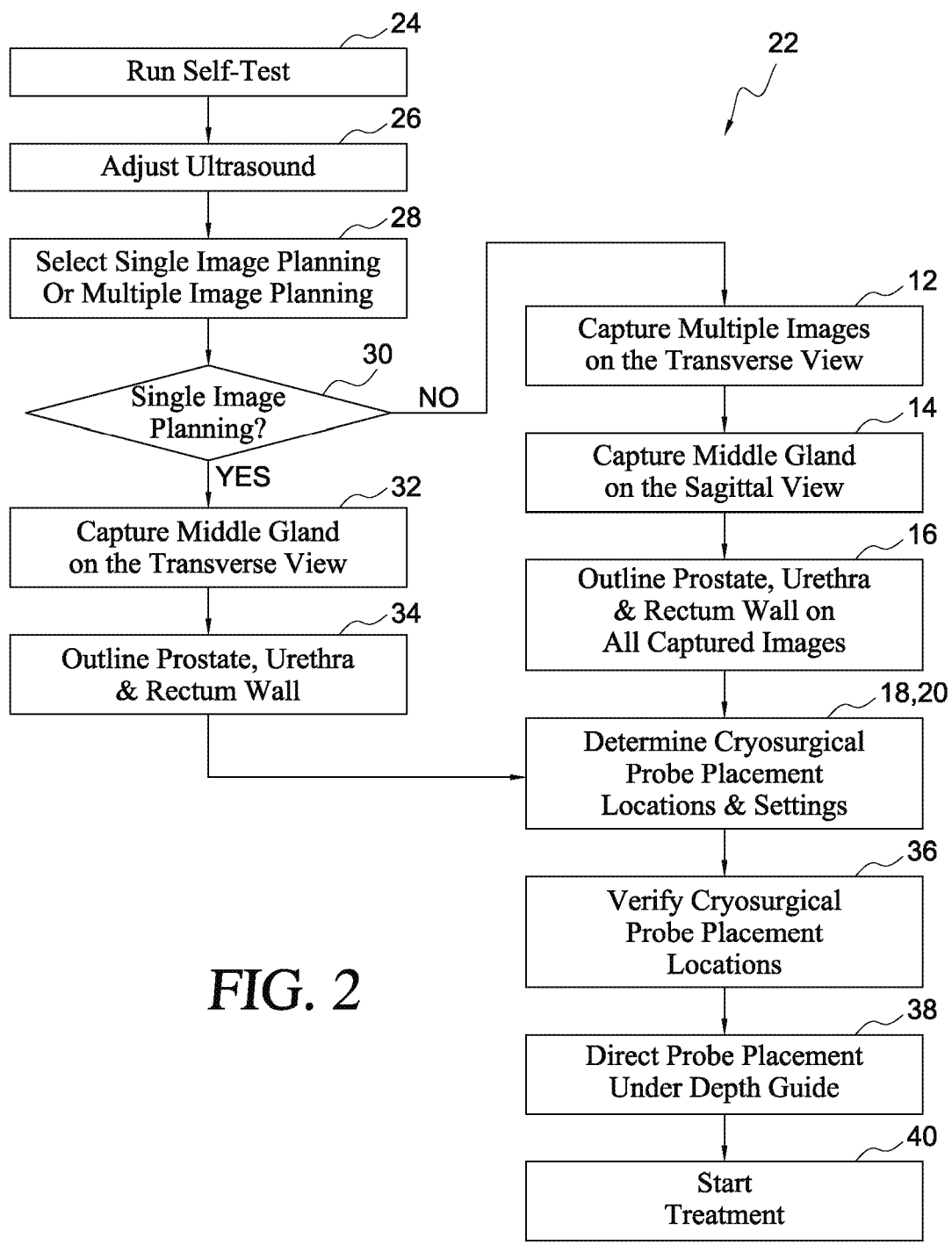
FIG. 2 is a more detailed flow chart of a preferred embodiment of the steps of the computer system.

Referring now to FIG. 2 a more detailed flow chart is presented, designated generally as 22, illustrating the steps provided by the computer system. Preliminary steps include running a pretest to assure system integrity (process block 24). A cryosurgical probe is dipped into sterilized liquid and then cryogenic fluid is passed through the cryosurgical probe. If the cryosurgical probe functions properly, no bubble should appear in the liquid and an iceball should form at the tip of the cryosurgical probe. A received ultrasound image is adjusted (process block 26) utilizing an ultrasound software system, as will be discussed in detail below. An option is then provided as to whether cryosurgical probe placement planning is to be provided using a single ultrasound image or multiple ultrasound images (process block 28).

If single image planning is selected (see decision block 30) the computer system confirms that single image planning has been selected and then captures the middle gland on the transverse view (process block 32). It then outlines the prostate, the urethra and the rectum wall on the transverse, middle gland view (process block 34).

If multiple image planning is selected (see decision block 30) the steps discussed with respect to FIG. 1 are applied. The computer system captures a plurality of transverse views of the prostate, as noted by numeral designation 12. It then captures a sagittal view of the prostate (process block 14). The capsule of the prostate, the urethra and the rectal wall of the patient are outlined with the assistance of the operator, utilizing the captured plurality of transverse views and the captured sagittal view (process block 16). A 3-dimensional model of the prostate, the urethra and the rectal wall is constructed utilizing the outlines noted above. The 3-dimensional model is used to determine i) the number of cryosurgical probes to be utilized; ii) probe settings; and, iii) probe placement positions. (See process blocks 18, 20.)

Cryosurgical probe placement locations are then verified (process block 36). A first criterion of verification is that each cryosurgical probe should be positioned at least 5 mm away from a periphery of a urethra. A second criterion of verification is that a cryosurgical probe should be positioned a safe margin away from a rectal wall. A third criterion of verification is that a distance between two cryosurgical probes that are next to each other should not exceed the sum of the radii of the lethal iceballs of the two cryosurgical probes. A fourth criterion of verification is that a distance from a cryosurgical probe to a periphery of a prostate should not exceed a radius of the lethal iceball of the cryosurgical probe. If all of these criteria are not simultaneously met, one or more of the least critical criteria may be compromised as desired to provide functionality.

Graphical depth guide software is utilized to direct probe placement under a depth guide (process block 38). This provides a graphical overlay on an ultrasound image of a sagittal view for assisting in the placement of cryosurgical probes. As will be discussed in detail below, the graphical overlay includes a scale and an icon of a cryosurgical probe. The icon is divided into two parts. The first part is colored in blue representing a length of the lethal ice of the variable cryosurgical probe. The second part is colored in while representing non-lethal ice of the variable cryosurgical probe. The distance from the graphical overlay to the surface of the ultrasound probe changes corresponding to the variable surgical probe selected. The lengths of the lethal ice and non-lethal ice change in a manner corresponding to a selected setting of the variable cryosurgical probe. The icon can be dragged and dropped horizontally along the scale. After determining the optimal location and the length of desired lethal ice by moving the depth guide, an operator can select a setting on a variable surgical probe accordingly then insert it into a patient along the graphical depth guide. Cryosurgical treatment is then commenced (process block 40).

Figure 3:
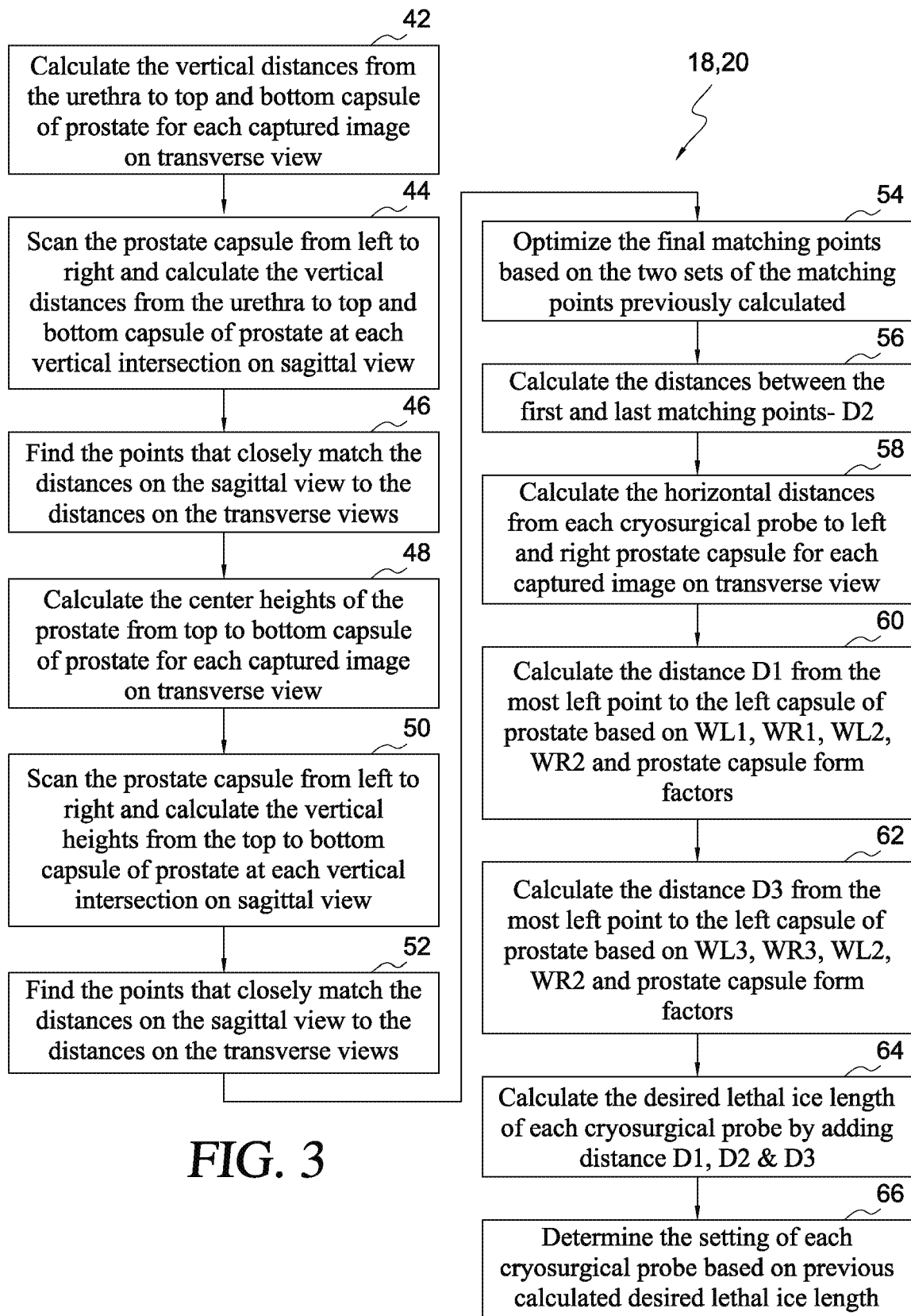
FIG. 3 is a flow chart of the probe placement algorithm of FIG. 2.

Referring now to FIG. 3 the determination, by the computer system, of variable probe settings is illustrated, designated generally as 18, 20. This involves constructing the 3-dimensional model and utilizing the 3-dimensional model to determine i) the number of cryosurgical probes to be utilized; ii) probe settings; and, iii) probe placement positions.

Figure 4A:
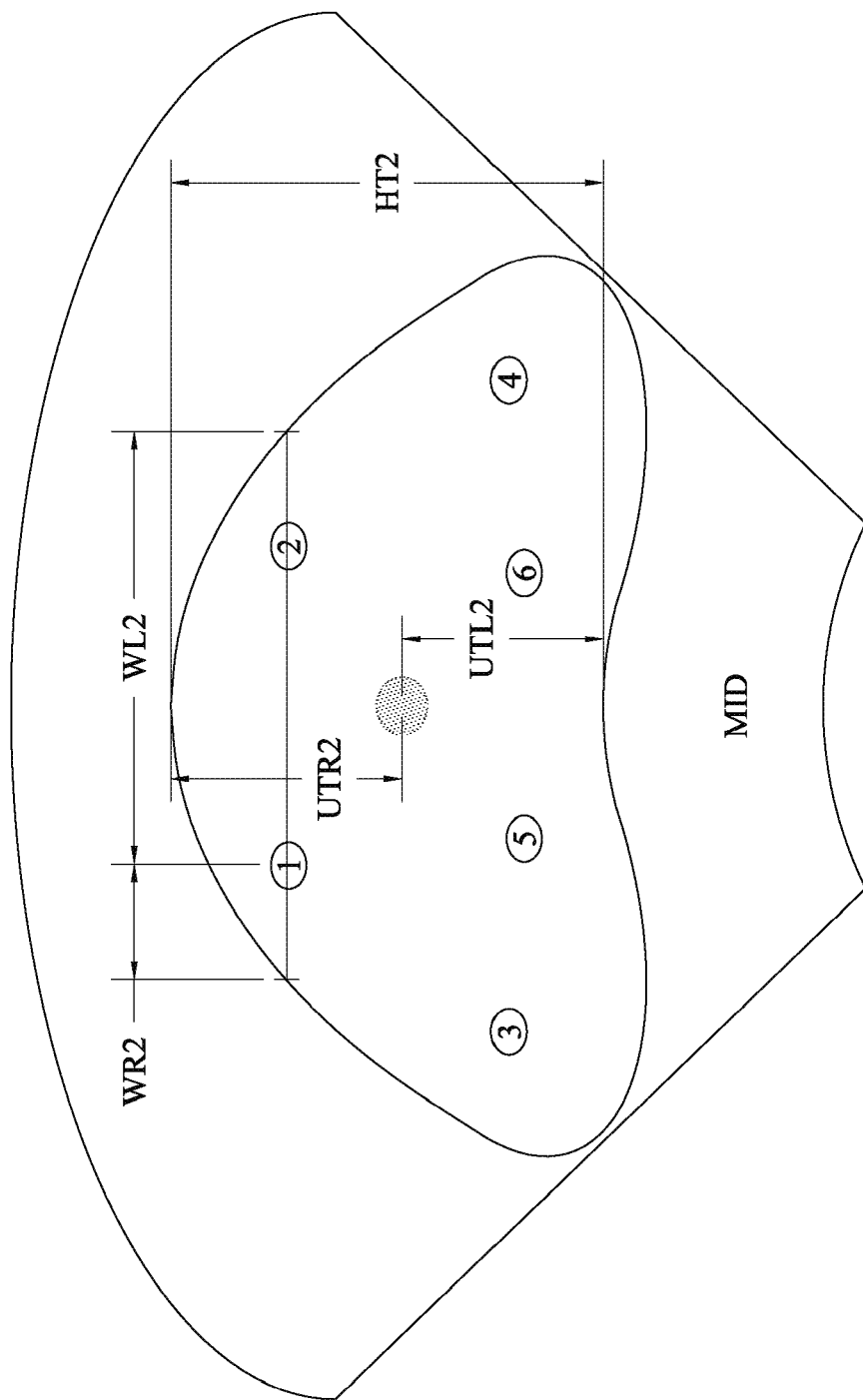
FIG. 4A is a schematic illustration of a transverse view of the prostate capsule showing parameters utilized by the computer system of the present invention, this transverse view being taken at a middle section of the prostate.
Figure 4B:
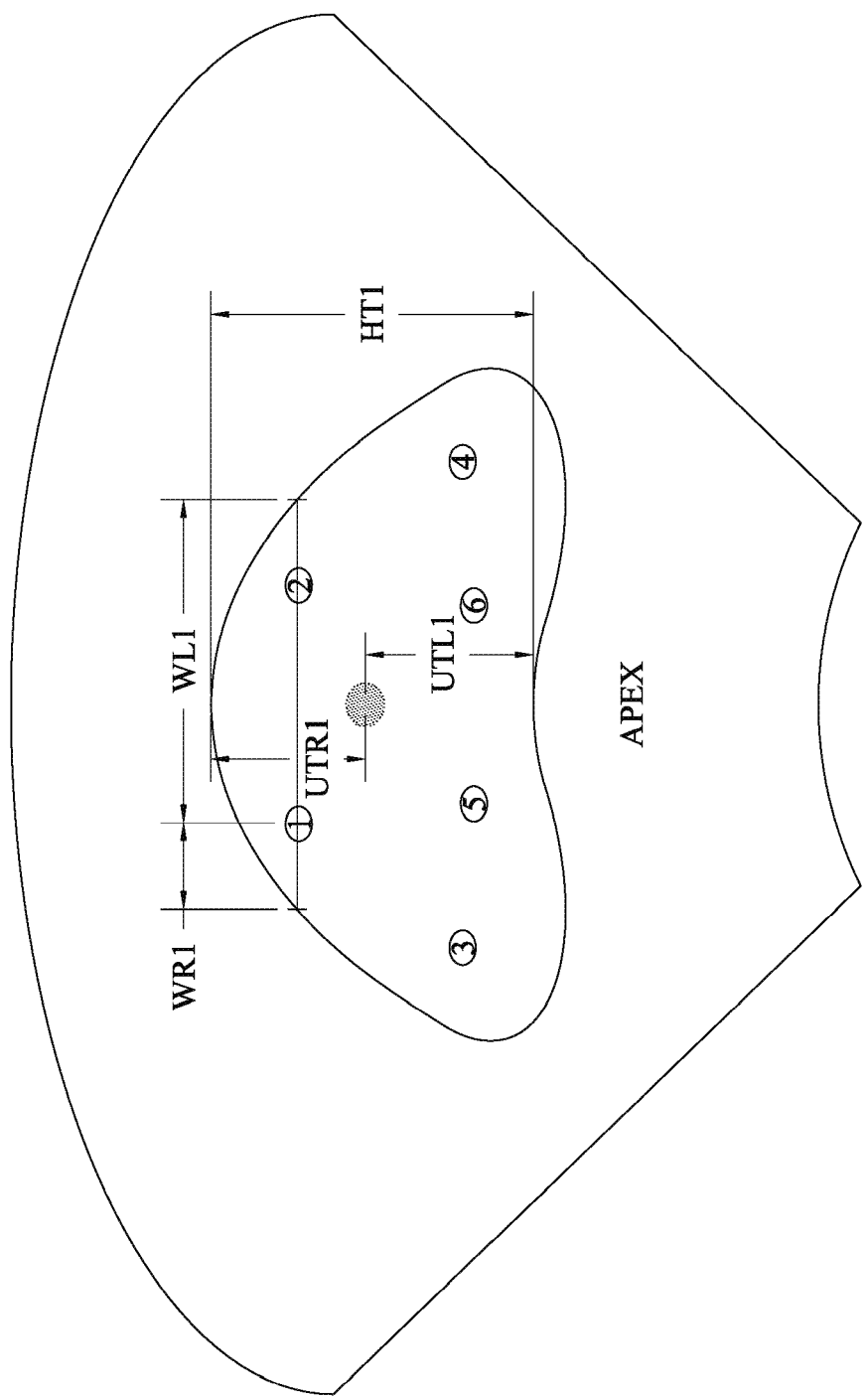
FIG. 4B is a schematic illustration of another transverse view of the prostate, this view being taken at the apex of the prostate.
Figure 4C:
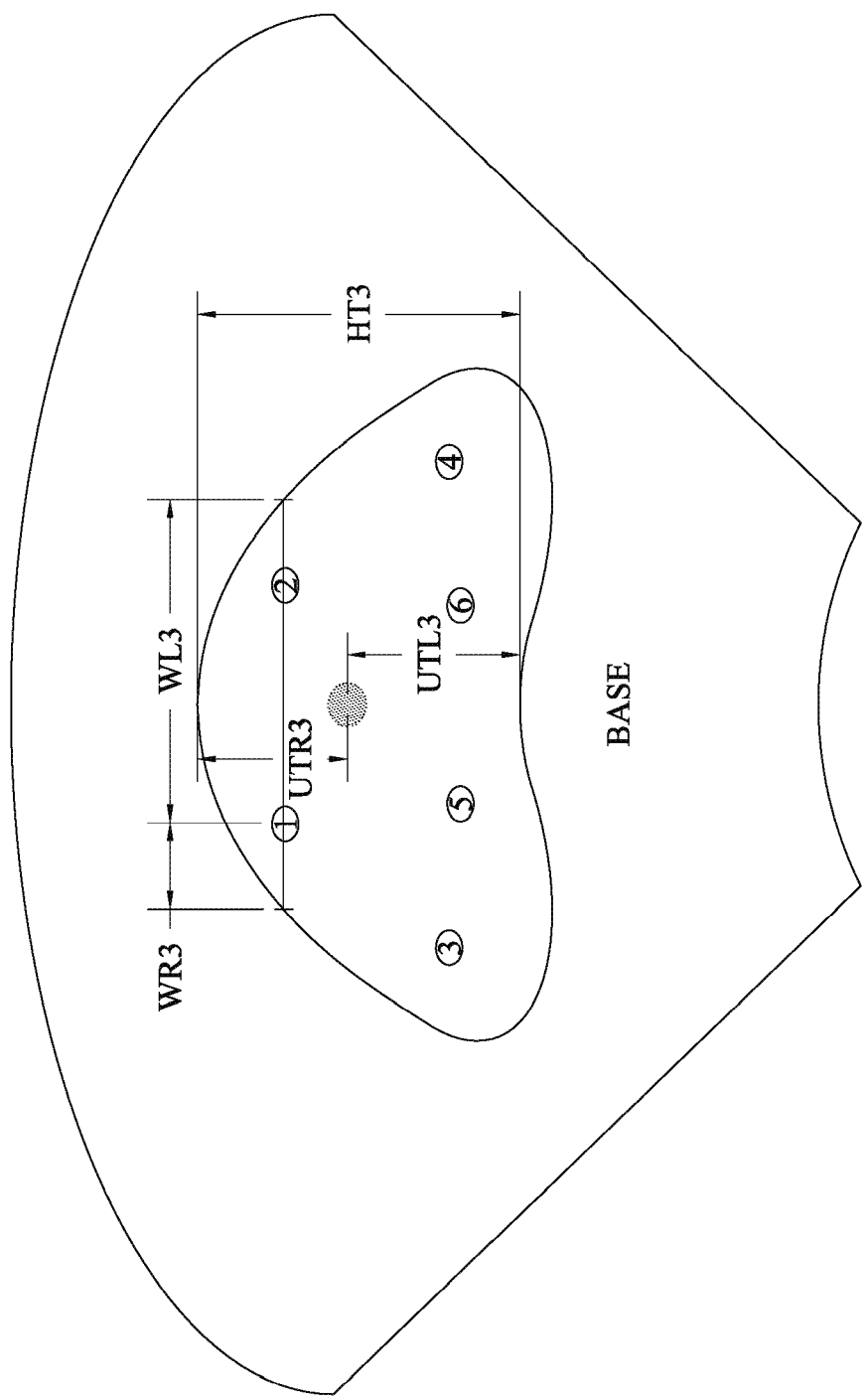
FIG. 4C is a schematic illustration of another transverse view of the prostate, this view being taken at the base of the prostate.

In a first step, vertical distances from the urethra to top and bottom capsules of the prostate are calculated for each captured transverse view (process block 42). Referring now to FIGS. 4A, 4B and 4C, transverse views of the prostate are shown along the largest (mid) section, the apex, and the base, respectively. At the apex, the vertical distance from the top of the capsule to the urethra is denoted as UTR1. At the largest section, the vertical distance from the top of the capsule to the urethra is denoted as UTR2. Similarly, at the base, the vertical distance from the top of the capsule to the urethra is denoted as UTR3. Although this example shows three sections captured, additional sections can be similarly captured and vertical distances (UTRn) calculated. Similar calculations of vertical distances from the urethra at the bottom of the prostate capsule are also provided as denoted UTL1, UTL2, UTL3.

Figure 5:
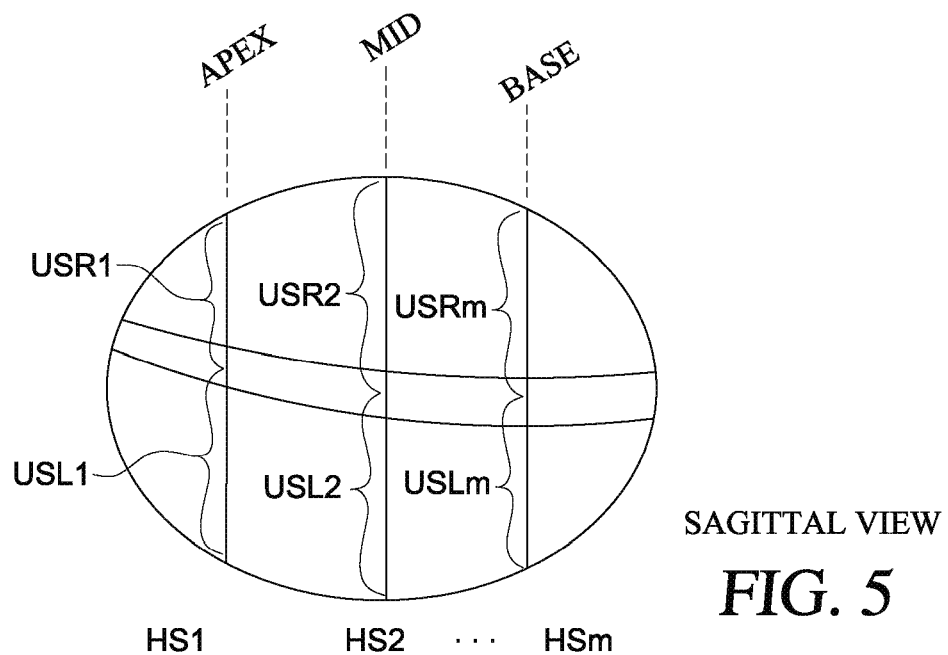
FIG. 5 is a schematic illustration of a sagittal view of the prostate taken at the center of the prostate.

The prostate capsule is then scanned on the sagittal view, from left to right, and the vertical distances from the urethra to the top and bottom capsule of the prostate at each vertical intersection on the sagittal view are calculated. As shown in FIG. 5 the sagittal view vertical distances are denoted as USR1, USR2, USR3 . . . USRm defining a USR list, and USL1, USL2, USL3 . . . USLm thus defining a USL list.

As can be seen in FIG. 3, process block 46, the software then finds the points that closely match the distances on the sagittal view to the distances on the transverse view. In other words, it finds a first of coordinates that closely match UTR1 from the USR list, UTL1 from the USL list, UTR2 from the USR list, UTL2 from the USL list, . . . UTRn from the USR list, UTLn from the USL list.

Next, as noted in process block 48, the software calculates the center heights of the prostate from the top to the bottom of the capsule of the prostate for each captured image on the transverse view, the transverse view center heights being denoted as HT1, HT2, HT3, . . . HTn. See also FIGS. 4A-4C.

As noted in process block 50, the prostate capsule is then scanned on the sagittal view and the vertical heights calculated from the top to the bottom of the capsule of the prostate, the sagittal view vertical heights being denoted as HS1, HS2, HS3, . . . HSm, defining an HS list. See also FIG. 5.

A second set coordinates that closely match HT1 from the HS list, HT2 from the HS list, . . . HTn from the HS list is then determined (process block 52). The software then utilizes the first set of coordinates and the second set of coordinates to calculate a final, optimized set of coordinates (process block 54).

The horizontal component, D2, of the distance between a first point of the optimized set of coordinates and a last point of the optimized set of coordinates, on the sagittal view, can then be calculated (process block 56).

Figure 6:
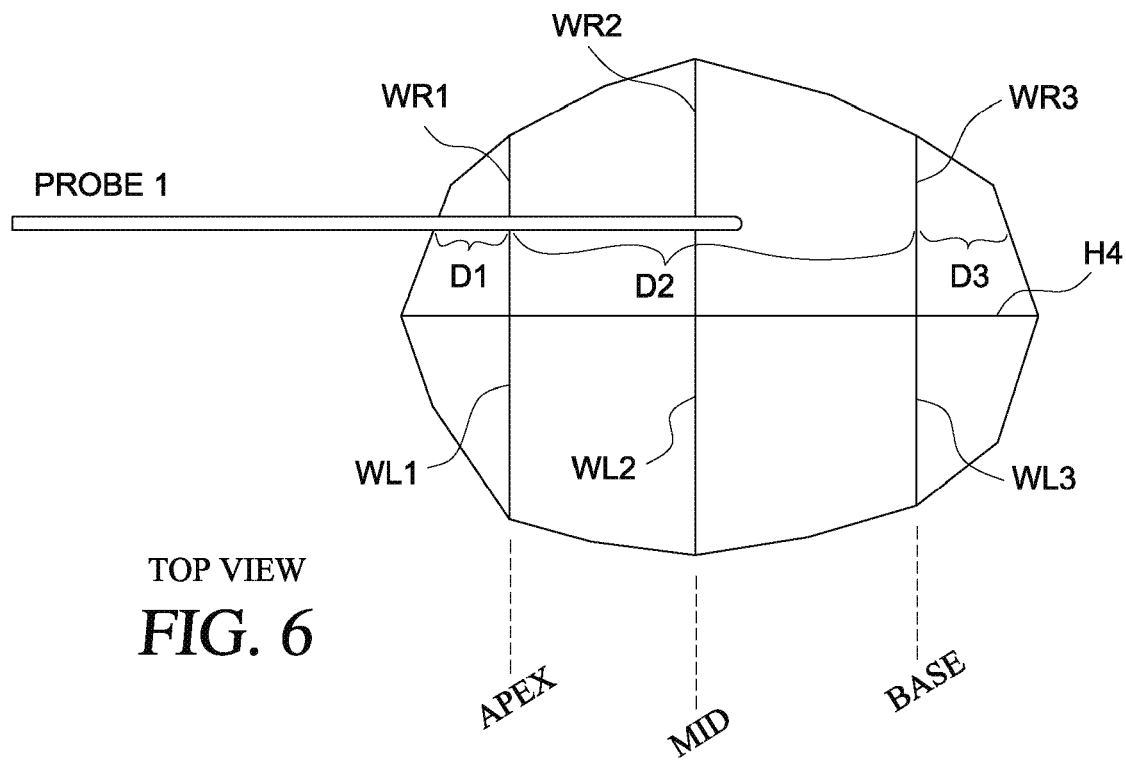
FIG. 6 is a schematic illustration of a top view of the prostate.

The horizontal components of the distances between each cryosurgical probe and the left of the prostate capsule are calculated for each transverse view, denoted as WR1, WR2, WR3, . . . WRn (process block 58). Similarly, the horizontal components of the distances between each cryosurgical probe and the right of the prostate capsule are calculated for each transverse view, denoted as WL1, WL2, WL3, . . . Wln. See also FIG. 6.

The software then utilizes selected WR1, WR2, WR3, . . . WRn; selected WL1, WL2, WL3, . . . Wln; and, D2 to calculate the distances, D1, from the first point of the optimized set of coordinates 6 and the left of the prostate capsule, on the transverse view (process block 60).

Selected WR1, WR2, WR3, . . . WRn; selected WL1, WL2, WL3, . . . Wln; and, D2 are utilized to calculate the distances, D3, from the last point of the optimized set of coordinates and the right of the prostate capsule, on the transverse view (process block 62).

D1, D2 and D3 are then utilized to determine the length of a resultant lethal ice produced by the cryosurgical probes (process block 64). Appropriate settings of the cryosurgical probes based on the length of the resultant lethal ice can then be determined (process block 66).

Referring now to FIG. 7, implementation of the computer system into a cryosurgical system is illustrated, the cryosurgical system being designated generally as 70. The cryosurgical system 70 includes a cryosurgical probe system, designated generally as 72. The cryosurgical probe system 72 includes a plurality of cryosurgical probes 74; a control system 76 operatively connected to the plurality of cryosurgical probes 74; and, a cryogenic fluid source 78 operatively connectable to the control system 76. It also includes temperature probes 80.

A temperature data acquisition system 82 acquires the temperature of selected locations in the vicinity of the prostate utilizing the temperature probes 80, cryosurgical probes 74 and the control system 76.

An imaging system, preferably an ultrasound system 84, and most preferably an integrated ultrasound system is utilized for obtaining selected images of selected locations in the vicinity of the prostate.

A computer system, designated generally as 86, is operatively connected to the cryosurgical probe system 72 and the ultrasound system 84. The computer system 86 implements the steps outlined above with respect to FIGS. 1-6. It includes an integrated data processing system 88, suitable computer input/output devices such as a computer monitor, keyboard and mouse (collectively denoted as 90) and a video output 92. The video output 92 is provided so that an operator can conveniently view the display at another location away from the computer monitor itself. A video input 94 is provided from an external ultrasound system if an integrated ultrasound system is not utilized. The ultrasound system software should be capable of adjusting contrast, brightness, gains, focus, depth, and imaging size of the ultrasound image. Furthermore, the ultrasound system software should be capable of measuring a plurality of dimensions on an ultrasound image and of changing ultrasound views by toggling ultrasound transducers.

The fluid source may be, for example, a cryosurgical system such as that manufactured by present assignee, Endocare, Inc., Irvine, Calif. Such a cryosurgical system typically utilizes argon gas from an argon gas source to provide Joule-Thomson cooling of the cryosurgical probes. Alternatively, nitrogen can be used. Alternatively, a fluid supply system can be utilized that does not require an external fluid supply source. Heating of the cryosurgical probes is typically provided by a helium gas source for providing a helium gas flow through the nozzle of the cryosurgical probe. This provides a heating effect. Such heating of the cryosurgical probes is provided to unstick the probes from the treated tissue for cryoprobe removal. The cryosurgical probes may be of the type manufactured by present assignee, Endocare, Inc., Irvine, Calif.

A preferred cryosurgical probe is a variable cryosurgical probe such as that disclosed and claimed in co-owned U.S. patent Ser. No. 11/613,054 filed Dec. 19, 2006 to Duong, et al. entitled "Cryosurgical Probe With Vacuum Insulation Tube Assembly," incorporated herein by reference in its entirety. Ser. No. 11/613,054 is assigned to present assignee, Endocare, Inc., Irvine, Calif.

Another variable cryosurgical probe is disclosed and claimed in co-owned U.S. Pat. Publication US 20050192565 (U.S. patent Ser. No. 11/116,873), to Eum et al. entitled "Detachable Cryosurgical Probe with Breakaway Handle," incorporated herein by reference in its entirety. Ser. No. 11/116,873 is also assigned to present assignee, Endocare, Inc., Irvine, Calif.

Other cryosurgical probes are described in U.S. Pat. Publication No. 20040267248 (U.S. Ser. No. 10/603,883) to Duong, et al., entitled Detachable Cryosurgical Probe, filed on Jun. 25, 2003, incorporated herein by reference in its entirety; and, U.S. Pat. Publication US 20050010200 (U.S. patent Ser. No. 10/828,031), to Damasco, et al. entitled "Detachable Cryosurgical Probe," incorporated herein by reference in its entirety.

U.S. Pat. No. 6,643,535 issued to Damasco, et al. entitled "System for Providing Computer Guided Ablation of Tissue," is also incorporated herein by reference in its entirety.

A heat exchanger or cryostat is utilized to provide heat exchange between inlet gas and outlet gas. Although the heat exchanger is preferably a coiled fin tube heat exchanger various other types of heat exchangers may be utilized such as a tube-in-tube sintered cryostat, threaded cryostat, coiled/sintered cryostat, or stacked coil cryostat. These different types of cryostats are disclosed and claimed in U.S. Pat. Publication No. 20050010200 (U.S. Ser. No. 10/828,031), entitled Detachable Cryosurgical Probe, filed on Apr. 20, 2004, discussed above.

FIG. 8, is a screenshot of a computer display using present Assignee's Cryocare CS™ System, this screenshot being designated generally as 96. In this screen shot, the user has finished an outline 98 of the prostate and an outline 100 of the urethra, and he is performing an outline 102 of the rectal wall. The user can drag each dot 103 around so that the outline can fit the shape of the rectal wall. This corresponds to process block 16 of FIG. 1.

Referring now to FIG. 9, another screen shot is illustrated, designated generally as 104 showing use of a depth guide. The computer system is programmed with graphical depth guide software, as discussed above, capable of providing a graphical overlay on an ultrasound image 106 for assisting in the placement of the cryosurgical probes. This depth guide display format includes a first, (i.e. horizontal) scale 108 having a plurality of spaced markers. The cryosurgical probe icon 110 represents a cryosurgical probe. The cryosurgical probe icon 110 is positioned adjacent to the first scale 108. The cryosurgical probe icon defines a kill zone 112 (typically colored blue) and a non-lethal zone 114 of the cryosurgical probe. The kill zone 112 represents a lethal temperature range and the non-lethal zone represents a temperature above the lethal temperature range. The kill zone 112 and non-lethal zone 114 cooperate with the spaced markers 108 to provide a visual guide for placing the cryosurgical probes. These zones are dependent on variable settings of the probe.

A second (i.e. vertical) scale 116 orthogonal to the first scale 108 has a second plurality of spaced markers. The position of the cryosurgical probe icon 110 on the second scale 116 defines the distance of the cryosurgical probe 110 from an ultrasound probe, by referring to the image 106.

Thus, in a broad aspect, the present invention is a cryosurgical system for assisting an operator in placing and operating cryosurgical probes in the prostate of a human patient, wherein the cryosurgical probes are inserted through the skin of the perinea! area of the patient and into the prostate. The cryosurgical system includes a treatment system, comprising a computer system which is programmed with software capable of optimizing the resultant ice produced by the cryosurgical probes for a specific patient. An ultrasound imaging system is integrated with the treatment system, wherein the computer software is programmed to adjust an ultrasound image.

Thus, while the preferred embodiments of the devices and methods have been described in reference to the environment in which they were developed, they are merely illustrative of the principles of the invention. For example, although ultrasound imaging has been described, certain applications may require guidance using various other imaging techniques such as CT guidance or MRI.

Other embodiments and configurations may be devised without departing from the spirit of the invention and the scope of the appended claims.

The invention claimed is:

1. A cryosurgical guide system for directing probe placement during a cryosurgical procedure, the system comprising:
    a computer configured to perform the following steps:
    receive at least one captured view of a region of interest in a patient;
    receive indicators to identify the region of interest and an area outside the region of interest based on the least one captured view;
    determine cryosurgical probe placement locations and cryosurgical probe settings for a plurality of cryosurgical probes to be used during the cryosurgical procedure; and
    verify the cryosurgical probe placement locations and the cryosurgical probe settings based on the indicators that identify the region of interest and the area outside the region of interest, and one or more criterion of verification, wherein
    the indicators are included in a graphical overlay on the at least one captured view, the graphical overlay including an outline of features of interest, a scale, and an icon representing placement of a cryosurgical probe with respect to the scale and the features of interest.

2. The cryosurgical guide system of claim 1, wherein the region of interest is located within an organ selected from the group consisting of a prostate, kidney, liver, and lung.

3. The cryosurgical guide system of claim 1, wherein the at least one captured view comprises a transverse view of the region of interest.

4. The cryosurgical guide system of claim 1, wherein the at least one captured view comprises a sagittal view of the region of interest.

5. The cryosurgical guide system of claim 1, wherein the at least one captured view is captured by an ultrasound imaging system in communication with the system.

6. The cryosurgical guide system of claim 1, wherein the at least one captured view is captured by a CT scan device or a MRI device.

7. The cryosurgical guide system of claim 1, wherein the computer is further configured to construct a 3-dimensional model of the region of interest and the area outside the region of interest on the at least one captured view and the received indicators.

8. The cryosurgical guide system of claim 1, wherein the indicators are received in response to an operator outlining one of a prostate, a urethra and a rectal wall on the at least one captured image.

9. The cryosurgical guide system of claim 1, wherein a first criterion of verification includes that each cryosurgical probe location is located at least a predetermined distance away from an organ or other structure in the patient.

10. The cryosurgical guide system of claim 1, wherein the cryosurgical probe icon defines a kill zone and a non-lethal zone.

11. The cryosurgical guide system of claim 1, wherein the scale includes a depth guide on an image of the region of interest and the area outside the region of interest.

12. A method for assisting an operator in placing and operating cryosurgical probes in a patient comprising:
receiving at least one captured view of a region of interest in a patient;
receiving indicators to identify the region of interest and an area outside the region of interest based on the at least one captured view;
determining cryosurgical probe placement locations and cryosurgical probe settings for a plurality of cryosurgical probes to be used during the cryosurgical procedure; and
verifying the cryosurgical probe placement locations and the cryosurgical probe settings based on the indicators that identify the region of interest and the area outside the region of interest, and one or more criterion of verification, wherein
the indicators are included in a graphical overlay on the at least one captured view, the graphical overlay including an outline of features of interest, a scale, and an icon representing placement of a cryosurgical probe with respect to the scale and the features of interest.

13. The method of claim 12, wherein the region of interest is located within an organ selected from the group consisting of a prostate, kidney, liver, and lung.

14. The method of claim 12, wherein the at least one captured view is captured by an ultrasound imaging system in communication with the system.

15. The method of claim 12, wherein the at least one captured view is captured by a CT scan device or a MRI device.

16. The method of claim 12, further comprising constructing a 3-dimensional model of the region of interest and the area outside the region of interest on the at least one captured view and the received indicators.

17. The method of claim 12, wherein the indicators are received in response to an operator outlining one of a prostate, a urethra and a rectal wall on the at least one captured image.

18. The method of claim 12, wherein a first criterion of verification includes that each cryosurgical probe location is located at least a predetermined distance away from an organ or other structure in the patient.

19. The method of claim 12, wherein the cryosurgical probe icon defines a kill zone and a non-lethal zone.

20. The method of claim 12, wherein the scale includes a depth guide on an image of the region of interest and the area outside the region of interest.

* * * * *